United States Patent [19]

Conine et al.

[11] Patent Number: 4,797,405
[45] Date of Patent: Jan. 10, 1989

[54] STABILIZED PERGOLIDE COMPOSITIONS

[75] Inventors: James W. Conine; Julian L. Stowers, both of Indianapolis, Ind.

[73] Assignee: Eli Lilly and Company, Indianapolis, Ind.

[21] Appl. No.: 112,360

[22] Filed: Oct. 26, 1987

[51] Int. Cl.$^4$ .................. A61K 31/48; C07D 457/02
[52] U.S. Cl. ......................................... 514/288; 546/67
[58] Field of Search ........................ 546/67; 514/288

[56] References Cited

U.S. PATENT DOCUMENTS

| | | | |
|---|---|---|---|
| 3,864,469 | 2/1975 | Reiser et al. | 514/168 |
| 4,166,182 | 8/1979 | Kornfeld et al. | 546/67 |
| 4,202,979 | 5/1980 | Kornfeld et al. | 546/67 |
| 4,329,366 | 5/1982 | Nashed et al. | 514/626 |
| 4,473,565 | 9/1984 | Rovee et al. | 514/174 |
| 4,547,505 | 10/1985 | Oepen et al. | 514/255 |

Primary Examiner—Donald G. Daus
Assistant Examiner—Cecilia Shen
Attorney, Agent, or Firm—Edward P. Gray; Leroy Whitaker

[57] ABSTRACT

Pharmaceutical compositions containing pergolide or a salt thereof stabilized to decomposition by light by incorporation therewith of a stabilizing agent selected from polyvinylpyrrolidone, α-tocopherol succinate and propyl gallate.

10 Claims, No Drawings

STABILIZED PERGOLIDE COMPOSITIONS

BACKGROUND OF THE INVENTION

Pergolide is an ergoline derivative which exhibits potent dopaminergic agonist activity and also decreases plasma prolactin concentrations. The compound is thus useful in treating physiological manifestations associated with hyperprolactinemia. Chemically, pergolide is D-6-n-propyl-8β-methylmercaptomethylergoline.

Pergolide is known to decompose upon exposure to light (apparently to a sulfoxide species) thus making it necessary to handle the compound and store the ultimate dosage form in light-controlled environments so as to avoid a demonstrable drop in potency of the therapeutic agent. In order to retard this drop in potency, certain stabilizing agents have been incorporated into pharmaceutical compositions containing pergolide which surprisingly reduce the decomposition of this compound when exposed to light.

SUMMARY OF THE INVENTION

The present invention is directed to a pharmaceutical composition of pergolide or a salt thereof stabilized to decomposition by light. Said composition comprises a therapeutically effective amount of pergolide or a salt thereof, a stabilizing agent selected from polyvinylpyrrolidone, α-tocopherol succinate and propyl gallate in an amount sufficient to effect stabilization to decomposition by light and pharmaceutically acceptable excipients.

Also disclosed is a method of stabilizing a pharmaceutical composition of pergolide or a salt thereof to decomposition by light. The method comprises incorporating into said pharmaceutical composition, in addition to a therapeutically effective amount of pergolide or a salt thereof and pharmaceutically acceptable excipients, a stablizing agent selected from polyvinylpyrrolidone, α-tocopherol succinate and propyl gallae in an amount sufficient to effect stablization to decomposition by light.

DETAILED DESCRIPTION OF THE INVENTION

Pergolide (i.e., D-6-n-propyl-8β-methylmercaptomethylergoline) may be prepared as described in U.S. Pat. No. 4,166,182, which is incorporated herein by reference. Briefly, methyl dihydrolysergate is treated with cyanogen bromide in an inert solvent such as chloroform, methylene dichloride, toluene, DMF and the like to form D-6-cyano-8β-methoxycarbonyl ergoline. The cyanide group is then readily removed as by zinc dust in acetic acid forming a secondary amine function at N-6 which can then be re-alkylated with, for example, N-propyl iodide in an inert, preferably polar solvent such as dimethylformamide or nitromethane at temperatures in the range of 20°-50° centigrade (C). The ester function at C-8 is then reduced by treatment with, for example, sodium borohydride in dioxane to form D-6-n-propyl-8β-hydroxymethylergoline which is then re-esterified by treatment with methanesulfonyl chloride in pyridine to form D-6-n-propyl-8β-mesyloxymethyl ergoline. The mesyloxy derivative is then treated with methylmercaptan in dimethyl acetate to render D-6-n-propyl-8β-methylmercaptomethylergoline (pergolide).

The above-noted U.S.patent discloses that various salts of pergolide may be prepared including acid addition salts of inorganic acids such as hydrochloric, nitric, phosphoric and sulfuric acids as well as salts derived from nontoxic organic acids. Such salts thus include sulfate, nitrate, phosphate, acetate, propionate, caprylate, oxalate, malonate, phenylacetate, citrate, lactate, malate, tartrate, maleate, methanesulfonate, toluenesulfonate and the like. For purposes of the present invention, a preferred salt is the methanesulfonate salt, prepared by treating D-6-n-propyl-8β-methylmercaptomethylergoline with methanesulfonic acid to yield D-6-n-propyl-8β-methylmercaptomethylergoline methanesulfonate or simply pergolide mesylate.

It has been found that pharmaceutical compositions of pergolide or a salt thereof may be stabilized to decomposition by light by the addition to said composition of a stabilizing agent selected from polyvinylpyrrolidone, α-tocopherol succinate or propyl gallate. Polyvinylpyrrolidone (also known as povidone or PVP) is a commercially available polymer of 1-ethenyl-2-pyrrolidinone which has been used in the past as a pharmaceutic aid as a dispersing or suspending agent. α-Tocopherol succinate is vitamin E acid succinate which may be prepared by treating α-tocopherol with succinic anhydride in pyridine. See U.S. Pat. No. 2,680,749 which is incorporated herein by reference. β-Tocopherol succinate is also a commercially available product. Likewise propyl gallate (i.e., 3,4,5-trihydroxybenzoic acid propyl ester) is a commercially available product or may be readily prepared by known methodologies. Preferably, the stabilizing agent used in the present invention is polyvinylpyrrolidone.

For purposes of the present invention, one or more (preferably one) of the stabilizing agents disclosed herein is present in the pharmaceutical composition in an amount sufficient to effect stabilization to decomposition by light of said composition. For polyvinylpyrrolidone this amount may vary from 0.3 to 2 percent by weight of the total composition and is preferably 0.5 to 1.5 percent by weight of the total composition. For α-tocopherol succinate and propyl gallate, this amount may vary from 0.15 to 0.7 percent by weight of the total composition and is preferably 0.3 to 0.5 percent by weight of the total composition. The precise amount of stabilizing agent to be used in a particular composition will, of course, vary depending upon the ultimate size of the dosage form, the specific dosage form chosen, the amount of pergolide present in the dosage form, and the like. Suffice it to say that the pharmaceutical composition will contain the stabilizing agent in an amount sufficient to effect stabilization to decomposition by light of said composition. That is, the composition will be less readily decomposed by light when one of the stabilizing agents disclosed herein is incorporated with said composition (i.e., will be stabilized to decomposition by light).

Further, the pharmaceutical compositions which are stabilized to decomposition by light contain a therapeutically effective amount of pergolide or a salt thereof. As used herein, the term "therapeutically effective" refers to that amount of pergolide or a salt thereof sufficient to deliver, in single or divided doses, 0.01 to 6 milligrams (mg) of pergolide per day to the subject being administered. In a preferred embodiment, when pergolide mesylate is the pergolide salt in the composition, it is present in an amount sufficient to deliver, in single or divided doses, 0.01 to 8 mg of pergolide per day to the subject being administered. The skilled artisan will readily recognize that the therapeutically effective amount may vary widely particularly where the route of administration and the particular salt or free base being employed are considerations. Of course, other factors such as the weight or age of the subject being treated as well as the time, frequency and specific pharmaceutical formulation employed in the administration are to be considered in determining the therapeutically effective amount in a given situation. This amount may be readily ascertained in a particular instance by the skilled artisan utilizing conventional dose titration techniques.

The pharmaceutical compositions of pergolide or a salt thereof stabilized to decomposition by light are preferably compositions for oral administration. Such compositions include any of the conventional solid or liquid dosage forms such as, for example, tablets, capsules, powders, suspensions, and the like including any sustained release preparations thereof. In addition to pergolide (or a salt thereof) and stabilizing agent, the pharmaceutical compositions of the present invention for oral administration utilize pharmaceutically acceptable excipients including, but not limited to, diluents, carriers, lubricants and the like such as glucose, lactose corn and potato starch, microcrystalline cellulose, sodium carboxymethylcellulose, ethyl cellulose, cellulose acetate, powdered gum tragacanth, gelatin, alginic acid, agar, stearic acid, sodium, calcium and magnesium stearates, sodium lauryl sulfate, sodium citrate, calcium carbonate, dicalcium phosphate among others; as well as various buffering agents, surfactants, emulsifiers, dispersing agents, flavoring agents and the like.

Preparation of the pharmaceutical compositions disclosed herein are readily achieved by one skilled in the art. Further, the skilled artisan will appreciate that the ultimate pharmaceutical composition may be provided in multiple or discrete, unit dose fashion with the latter being preferred. In addition to the information provided herein pertinent to the preparation of the pharmaceutical compositions of the invention, further reference may be obtained from standard treatises such as *Remington's Pharmaceutical Sciences*, Seventeenth Edition, Mack Publishing Co., Easton, PA. (1985) which is incorporated herein by reference.

The invention will now be illustrated by the following examples which shall not be construed as a limitation thereon.

EXAMPLE 1

Table I depicts tablet formulations containing pergolide mesylate and one of the following stabilizing agents: polyvinylpyrrolidone (composition numbers 1 and 2); α-tocopherol succinate (composition number 3); and propyl gallate (composition number 4). Composition number 5 is a control where no stabilizing agent was incorporated into the formulation.

TABLE I[a]

| Ingredients | Composition No. | | | | |
| --- | --- | --- | --- | --- | --- |
| | 1 | 2 | 3 | 4 | 5 |
| Pergolide mesylate | 0.035 | 0.035 | 0.035 | 0.035 | 0.035 |
| Polyvinylpyrrolidone | 4.0 | 4.0 | — | — | — |
| α-tocopherol succinate | — | — | 1.0 | — | — |
| Propyl gallate | — | — | — | 1.0 | — |
| Lactose | 294.3 | 288.3 | 291.3 | 291.3 | 298.3 |
| Iron oxide yellow | 0.13 | 0.13 | 0.13 | 0.13 | 0.13 |
| Croscarmellose sodium | — | 6.0 | 6.0 | 6.0 | — |

TABLE I[a]-continued

| Ingredients | Composition No. | | | | |
| --- | --- | --- | --- | --- | --- |
| | 1 | 2 | 3 | 4 | 5 |
| Magnesium stearate | 1.535 | 1.535 | 1.535 | 1.75 | 1.535 |

[a]All amounts shown are in milligrams

These formulations and the compressed tablets made therefrom were prepared as follows. The lactose, iron oxide yellow and croscarmellose sodium were blended together and granulated with a hydroalcoholic solution of pergolide mesylate and the selected stabilizing agent (i.e., polyvinylpyrrolidone, α-tocopherol succinate or propyl gallate). The resultant granulation was dried, screened and blended with magnesium stearate and compressed into tablets weighing 300 mg each.

Tablets from each of the five compositions shown in Table I were exposed to fluorescent lights placed at a height of six inches from the tablets and maintained for seven days. However, prior to exposure, sample tablets from each of the five composition batches were assayed for pergolide content by high performance liquid chromatography (HPLC) as follows. One tablet (or the weight of ground composite tablets equivalent to the average weight of one tablet) was dissolved in a mixture of methanol and 0.1 normal HCl (80:20, respectively) by shaking for one hour. The resulting mixture was centrifuged and the clear supernatant was sampled (and further diluted according to tablet potency) and the samples were run on HPLC. The amount of pergolide per tablet was determined by comparing the area under the pergolide peak with standard peak areas obtained using known dilutions of pergolide mesylate reference standard.

After exposure to light for seven days, the exposed tablets were again assayed for pergolide content so as to determine the amount of decomposition which occurred during that period of time. The results are shown in Table II wherein Assay I refers to the tablet assay prior to exposure to light and Assay II refers to the assay of the tablets after exposure to light for seven days.

TABLE II[a]

| | Composition No. | | | | |
| --- | --- | --- | --- | --- | --- |
| Assay No. | 1 | 2 | 3 | 4 | 5 |
| I | 18.6 | 20.2 | 21.6 | 28.3 | 22.0 |
| II | 19.4 | 18.5 | 20.4 | 25.6 | 13.9 |
| Percent Change | +4.3 | −8.4 | −5.6 | −9.5 | −36.8 |

[a]All amounts shown (except for percent change) are in micrograms

As can be seen from the data presented in Table II, all compositions having a stabilizing agent included in the formulation all exhibited less than a 10 percent decrease in pergolide content following seven days of exposure to the fluorescent lighting. By contrast, composition number 5 which did not contain a stabilizing agent exhibited a decrease in pergolide content of nearly 37 percent.

EXAMPLE 2

Tablets of pergolide mesylate having the following compositions (amounts shown in milligrams) were prepared as described in Example 1.

|  | Composition No. | |
| Ingredients | 6 | 7 |
| --- | --- | --- |
| Pergolide mesylate | 0.0705 | 0.0705 |
| Polyvinylpyrrolidone | 4.0 | — |
| Lactose | 288.0 | 292.0 |
| Iron oxide yellow | 0.13 | 0.13 |
| Croscarmellose sodium | 6.0 | 6.0 |
| Magnesium stearate | 1.75 | 1.75 |

Again, following the procedures of Example 1, samples of tablets from batches of composition numbers 6 and 7 were exposed to fluorescent lights placed at a height of six inches and maintained for seven days. The same assays were performed as described in the previous example (i.e., assays for pergolide content before and after light exposure) as well as an assay for pergolide sulfoxide content (a major oxidation product of pergolide) before and after exposure to light. The assay for pergolide sulfoxide was conducted essentially as described above for pergolide (i.e., HPLC) but using a pergolide sulfoxide reference standard. The results of the assays for pergolide content and pergolide sulfoxide content are set forth in Tables III and IV, respectively.

TABLE III[a]

| | Pergolide Content | |
| | Composition No. | |
| | 6 | 7 |
| --- | --- | --- |
| Assay No. | | |
| I | 47.1 | 50.3 |
| II | 44.1 | 39.0 |
| Percent Change | −6.4 | −22.5 |

[a]All amounts shown (except for percent change) are expressed in micrograms.

TABLE IV[a]

| | Pergolide Sulfoxide Content | |
| | Composition No. | |
| | 6 | 7 |
| --- | --- | --- |
| Assay No. | | |
| I | 11.6 | 1.99 |
| II | 11.1 | 13.1 |
| Percent Change | −4.3 | +558 |

[a]All amounts shown (except for percent change) are expressed as a percent of pergolide concentration.

The data shown in Table III again clearly depict that compositions of pergolide mesylate containing, in this case, polyvinylpyrrolidone are stabilized to decomposition by light compared to a composition not containing the stabilizing agent. The results of the pergolide sulfoxide assays (Table IV) show a significant increase in sulfoxide content (as the product of decomposition) for formulation number 7. The data for composition number 6 are believed to be artifactual owing to the atypically high amount of pergolide sulfoxide present in the composition prior to exposure to the fluorescent lighting.

We claim:

1. A pharmaceutical composition of pergolide or a salt thereof stabilized to decomposition by light comprising a therapeutically effective amount of pergolide or a salt thereof, a stabilizing agent selected from polyvinylpyrrolidone, α-tocopherol succinate and propyl gallate in an amount sufficient to effect stabilization to decomposition by light and pharmaceutically acceptable excipients.

2. The pharmaceutical composition of claim 1 wherein the pergolide is present as pergolide mesylate.

3. The pharmaceutical composition of claim 2 wherein the stabilizing agent is polyvinylpyrrolidone.

4. The pharmaceutical composition of claim 3 wherein the polyvinylpyrrolidone is present in said composition in an amount of from 0.3 to 2 percent by weight of the total composition.

5. The pharmaceutical composition of claim 4 wherein the polyvinylpyrrolidone is present in said composition in an amount of from 0.5 to 1.5 percent by weight of the total composition.

6. A method of stabilizing a pharmaceutical composition of pergolide or a salt thereof to decomposition by light comprising incorporating into said pharmaceutical composition, in addition to a therapeutically effective amount of said pergolide or a salt thereof and pharmaceutically acceptable excipients, a stabilizing agent selected from polyvinylpyrrolidone, α-tocopherol succinate and propyl gallate in an amount sufficient to effect stabilization to decomposition by light.

7. The method of claim 6 wherein the pergolide is present as pergolide mesylate.

8. The method of claim 7 wherein the stabilizing agent is polyvinylpyrrolidone.

9. The method of claim 8 wherein the polyvinylpyrrolidone is present in an amount of from 0.3 to 2 percent by weight of the total composition.

10. The method of claim 9 wherein the polyvinylpyrrolidone is present in an amount of from 0.5 to 1.5 percent by weight of the total composition.

* * * * *